United States Patent
Cain et al.

(10) Patent No.: US 8,539,813 B2
(45) Date of Patent: Sep. 24, 2013

(54) GEL PHANTOMS FOR TESTING CAVITATIONAL ULTRASOUND (HISTOTRIPSY) TRANSDUCERS

(75) Inventors: Charles A. Cain, Ann Arbor, MI (US); Zhen Xu, Ann Arbor, MI (US); Adam Maxwell, Ann Arbor, MI (US); Tzu-Yin Wang, Taichung (TW); Simone Park, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 445 days.

(21) Appl. No.: 12/887,705

(22) Filed: Sep. 22, 2010

(65) Prior Publication Data

US 2011/0067624 A1  Mar. 24, 2011

Related U.S. Application Data

(60) Provisional application No. 61/244,619, filed on Sep. 22, 2009.

(51) Int. Cl.
*A61B 8/00* (2006.01)
*A61N 7/00* (2006.01)

(52) U.S. Cl.
USPC ............... 73/1.86; 73/866.4; 436/8; 600/439

(58) Field of Classification Search
CPC ...................... A61B 8/587; A61B 2017/00716
USPC ............ 73/1.82, 1.86, 649, 866.4; 422/536; 434/272; 436/8; 600/427, 437, 438, 439, 600/458; 116/201, 203
See application file for complete search history.

(56) References Cited

U.S. PATENT DOCUMENTS

| | | | |
|---|---|---|---|
| 3,679,021 A | 7/1972 | Goldberg et al. |
| 4,024,501 A | 5/1977 | Herring et al. |
| 4,117,446 A | 9/1978 | Alais |
| 4,269,174 A | 5/1981 | Adair |

(Continued)

FOREIGN PATENT DOCUMENTS

| | | |
|---|---|---|
| DE | 3544628 A1 | 6/1987 |
| DE | 3817094 A1 | 11/1989 |

(Continued)

OTHER PUBLICATIONS

Hall et al.; Imaging feedback of tissue liquefaction (histotripsy) in ultrasound surgery; IEEE Ultrasonic Symposium, Sep. 18-21, 2005, pp. 1732-1734.

(Continued)

*Primary Examiner* — R. A. Smith
(74) *Attorney, Agent, or Firm* — Shay Glenn LLP (57) ABSTRACT

A cavitational ultrasound (e.g., Histotripsy) gel phantom and cavitational ultrasound testing system are provided that may include any of a number of features. One feature of the phantom and system is that it can allow for instant visual feedback on the efficacy and dosage of a Histotripsy transducer. The changes in the gel phantom can be visualized with the naked eye without having to wait for histology. The changes in the gel phantom can also be visualized with a camera, with ultrasound imaging, or with microscopy. In various embodiments, the phantom includes indicators such as carbon particles, dye-encapsulated beads, and red blood cells. Methods associated with use of the cavitational ultrasound gel phantom and testing system are also covered.

41 Claims, 5 Drawing Sheets

(56) References Cited

U.S. PATENT DOCUMENTS

| | | | | |
|---|---|---|---|---|
| 4,277,367 A | * | 7/1981 | Madsen et al. | 436/8 |
| 4,351,038 A | | 9/1982 | Alais | |
| 4,406,153 A | * | 9/1983 | Ophir et al. | 73/1.86 |
| 4,440,025 A | | 4/1984 | Hayakawa et al. | |
| 4,453,408 A | * | 6/1984 | Clayman | 73/1.86 |
| 4,483,345 A | | 11/1984 | Miwa | |
| 4,549,533 A | | 10/1985 | Cain et al. | |
| 4,550,606 A | | 11/1985 | Drost | |
| 4,622,972 A | | 11/1986 | Giebeler, Jr. | |
| 4,641,378 A | | 2/1987 | McConnell et al. | |
| 4,689,986 A | | 9/1987 | Carson et al. | |
| 4,757,820 A | | 7/1988 | Itoh | |
| 4,791,915 A | | 12/1988 | Barsotti et al. | |
| 4,819,621 A | | 4/1989 | Ueberle et al. | |
| 4,829,491 A | | 5/1989 | Saugeon et al. | |
| 4,856,107 A | | 8/1989 | Dory | |
| 4,865,042 A | | 9/1989 | Umemura et al. | |
| 4,888,746 A | | 12/1989 | Wurster et al. | |
| 4,890,267 A | | 12/1989 | Rudolph | |
| 4,922,917 A | | 5/1990 | Dory | |
| 4,938,217 A | | 7/1990 | Lele | |
| 4,991,151 A | | 2/1991 | Dory | |
| 4,995,012 A | | 2/1991 | Dory | |
| RE33,590 E | | 5/1991 | Dory | |
| 5,014,686 A | * | 5/1991 | Schafer | 601/4 |
| 5,065,751 A | | 11/1991 | Wolf | |
| 5,080,101 A | | 1/1992 | Dory | |
| 5,080,102 A | | 1/1992 | Dory | |
| 5,091,893 A | | 2/1992 | Smith et al. | |
| 5,092,336 A | | 3/1992 | Fink | |
| 5,097,709 A | | 3/1992 | Masuzawa et al. | |
| 5,111,822 A | | 5/1992 | Dory | |
| 5,143,073 A | | 9/1992 | Dory | |
| 5,143,074 A | | 9/1992 | Dory | |
| 5,150,711 A | | 9/1992 | Dory | |
| 5,158,070 A | | 10/1992 | Dory | |
| 5,158,071 A | | 10/1992 | Umemura et al. | |
| 5,163,421 A | | 11/1992 | Bernstein et al. | |
| 5,209,221 A | | 5/1993 | Riedlinger | |
| 5,215,680 A | | 6/1993 | D'Arrigo | |
| 5,219,401 A | | 6/1993 | Cathignol et al. | |
| 5,230,340 A | | 7/1993 | Rhyne | |
| 5,295,484 A | | 3/1994 | Marcus et al. | |
| 5,316,000 A | | 5/1994 | Chapelon et al. | |
| 5,354,258 A | | 10/1994 | Dory | |
| 5,380,411 A | | 1/1995 | Schlief | |
| 5,409,002 A | | 4/1995 | Pell | |
| 5,431,621 A | | 7/1995 | Dory | |
| 5,435,311 A | | 7/1995 | Umemura et al. | |
| 5,443,069 A | | 8/1995 | Schaetzle | |
| 5,469,852 A | | 11/1995 | Nakamura et al. | |
| 5,474,071 A | | 12/1995 | Chapelon et al. | |
| 5,474,531 A | | 12/1995 | Carter | |
| 5,501,655 A | | 3/1996 | Rolt et al. | |
| 5,520,188 A | | 5/1996 | Hennige et al. | |
| 5,523,058 A | | 6/1996 | Umemura et al. | |
| 5,524,620 A | | 6/1996 | Rosenschein | |
| 5,540,909 A | | 7/1996 | Schutt | |
| 5,542,935 A | | 8/1996 | Unger et al. | |
| 5,558,092 A | | 9/1996 | Unger et al. | |
| 5,563,346 A | | 10/1996 | Bartelt et al. | |
| 5,566,675 A | | 10/1996 | Li et al. | |
| 5,573,497 A | | 11/1996 | Chapelon | |
| 5,580,575 A | | 12/1996 | Unger et al. | |
| 5,582,578 A | | 12/1996 | Zhong et al. | |
| 5,590,657 A | | 1/1997 | Cain et al. | |
| 5,601,526 A | | 2/1997 | Chapelon et al. | |
| 5,617,862 A | | 4/1997 | Cole et al. | |
| 5,648,098 A | | 7/1997 | Porter | |
| 5,666,954 A | | 9/1997 | Chapelon et al. | |
| 5,676,692 A | | 10/1997 | Sanghvi et al. | |
| 5,678,554 A | | 10/1997 | Hossack et al. | |
| 5,694,936 A | | 12/1997 | Fujimoto et al. | |
| 5,695,460 A | | 12/1997 | Siegel et al. | |
| 5,717,657 A | | 2/1998 | Ruffa | |
| 5,724,972 A | | 3/1998 | Petrofsky | |
| 5,743,863 A | | 4/1998 | Chapelon | |
| 5,759,162 A | | 6/1998 | Oppelt et al. | |
| 5,769,790 A | | 6/1998 | Watkins et al. | |
| 5,797,848 A | | 8/1998 | Marian et al. | |
| 5,823,962 A | | 10/1998 | Schaetzle et al. | |
| 5,827,204 A | | 10/1998 | Grandia et al. | |
| 5,836,896 A | | 11/1998 | Rosenschein | |
| 5,849,727 A | | 12/1998 | Porter et al. | |
| 5,873,902 A | | 2/1999 | Sanghvi et al. | |
| 5,879,314 A | | 3/1999 | Peterson et al. | |
| 5,932,807 A | | 8/1999 | Mallart | |
| 5,947,904 A | | 9/1999 | Hossack et al. | |
| 6,001,069 A | | 12/1999 | Tachibana et al. | |
| 6,022,309 A | | 2/2000 | Celliers et al. | |
| 6,036,667 A | | 3/2000 | Manna et al. | |
| 6,088,613 A | | 7/2000 | Unger | |
| 6,093,883 A | | 7/2000 | Sanghvi et al. | |
| 6,113,558 A | | 9/2000 | Rosenschein et al. | |
| 6,126,607 A | | 10/2000 | Whitmore, III et al. | |
| 6,128,958 A | | 10/2000 | Cain | |
| 6,143,018 A | | 11/2000 | Beuthan et al. | |
| 6,176,842 B1 | | 1/2001 | Tachibana et al. | |
| 6,308,585 B1 | | 10/2001 | Nilsson et al. | |
| 6,308,710 B1 | | 10/2001 | Silva | |
| 6,309,355 B1 | | 10/2001 | Cain et al. | |
| 6,318,146 B1 | * | 11/2001 | Madsen et al. | 73/1.86 |
| 6,321,109 B2 | | 11/2001 | Ben-Haim et al. | |
| 6,344,489 B1 | | 2/2002 | Spears | |
| 6,391,020 B1 | | 5/2002 | Kurtz et al. | |
| 6,413,216 B1 | | 7/2002 | Cain et al. | |
| 6,419,648 B1 | | 7/2002 | Vitek et al. | |
| 6,470,204 B1 | | 10/2002 | Uzgiris et al. | |
| 6,488,639 B1 | | 12/2002 | Ribault et al. | |
| 6,490,469 B2 | | 12/2002 | Candy | |
| 6,500,141 B1 | | 12/2002 | Irion et al. | |
| 6,506,154 B1 | | 1/2003 | Ezion et al. | |
| 6,506,171 B1 | | 1/2003 | Vitek et al. | |
| 6,508,774 B1 | | 1/2003 | Acker et al. | |
| 6,511,428 B1 | | 1/2003 | Azuma et al. | |
| 6,511,444 B2 | | 1/2003 | Hynynen et al. | |
| 6,522,142 B1 | | 2/2003 | Freundlich | |
| 6,524,251 B2 | | 2/2003 | Rabiner et al. | |
| 6,543,272 B1 | | 4/2003 | Vitek | |
| 6,559,644 B2 | | 5/2003 | Froundlich et al. | |
| 6,576,220 B2 | | 6/2003 | Unger | |
| 6,599,288 B2 | | 7/2003 | Maguire et al. | |
| 6,607,498 B2 | | 8/2003 | Eshel | |
| 6,612,988 B2 | | 9/2003 | Maor et al. | |
| 6,613,004 B1 | | 9/2003 | Vitek et al. | |
| 6,613,005 B1 | | 9/2003 | Friedman et al. | |
| 6,626,854 B2 | | 9/2003 | Friedman et al. | |
| 6,626,855 B1 | | 9/2003 | Weng et al. | |
| 6,635,486 B2 | * | 10/2003 | Madsen et al. | 436/8 |
| 6,645,162 B2 | | 11/2003 | Friedman et al. | |
| 6,648,839 B2 | | 11/2003 | Manna et al. | |
| 6,666,833 B1 | | 12/2003 | Friedman et al. | |
| 6,685,640 B1 | | 2/2004 | Fry et al. | |
| 6,685,657 B2 | | 2/2004 | Jones | |
| 6,705,994 B2 | | 3/2004 | Vortman et al. | |
| 6,719,449 B1 | | 4/2004 | Laugharn, Jr. et al. | |
| 6,719,694 B2 | | 4/2004 | Weng et al. | |
| 6,735,461 B2 | | 5/2004 | Vitek et al. | |
| 6,736,814 B2 | | 5/2004 | Manna et al. | |
| 6,770,031 B2 | | 8/2004 | Hynynen et al. | |
| 6,790,180 B2 | | 9/2004 | Vitek | |
| 6,852,082 B2 | | 2/2005 | Strickberger et al. | |
| 6,869,439 B2 | | 3/2005 | White et al. | |
| 6,890,332 B2 | | 5/2005 | Truckai et al. | |
| 6,929,609 B2 | | 8/2005 | Asafusa | |
| 7,004,282 B2 | | 2/2006 | Manna et al. | |
| 7,059,168 B2 | * | 6/2006 | Hibi et al. | 73/1.86 |
| 7,128,711 B2 | | 10/2006 | Medan et al. | |
| 7,128,719 B2 | | 10/2006 | Rosenberg | |
| 7,175,596 B2 | | 2/2007 | Vitek et al. | |
| 7,223,239 B2 | | 5/2007 | Schulze et al. | |
| 7,258,674 B2 | | 8/2007 | Cribbs et al. | |
| 7,273,458 B2 | | 9/2007 | Prausnitz et al. | |
| 7,273,459 B2 | | 9/2007 | Desilets et al. | |

| | | |
|---|---|---|
| 7,300,414 B1 | 11/2007 | Holland et al. |
| 7,311,679 B2 | 12/2007 | Desilets et al. |
| 7,331,951 B2 | 2/2008 | Eshel et al. |
| 7,341,569 B2 | 3/2008 | Soltani et al. |
| 7,347,855 B2 | 3/2008 | Eshel et al. |
| 7,358,226 B2 | 4/2008 | Dayton et al. |
| 7,367,948 B2 | 5/2008 | O'Donnell et al. |
| 7,374,551 B2 | 5/2008 | Liang et al. |
| 7,377,900 B2 | 5/2008 | Vitek et al. |
| 7,442,168 B2 | 10/2008 | Novak et al. |
| 7,462,488 B2 * | 12/2008 | Madsen et al. ............... 436/8 |
| 7,559,905 B2 | 7/2009 | Kagosaki et al. |
| 7,656,638 B2 | 2/2010 | Laakso et al. |
| 2001/0039420 A1 | 11/2001 | Burbank et al. |
| 2001/0041163 A1 | 11/2001 | Sugita et al. |
| 2002/0045890 A1 | 4/2002 | Celliers et al. |
| 2002/0078964 A1 | 6/2002 | Kovac et al. |
| 2002/0099356 A1 | 7/2002 | Unger et al. |
| 2003/0092982 A1 | 5/2003 | Eppstein |
| 2003/0112922 A1 | 6/2003 | Burdette et al. |
| 2003/0157025 A1 | 8/2003 | Unger et al. |
| 2003/0221561 A1 | 12/2003 | Milo |
| 2004/0060340 A1* | 4/2004 | Hibi et al. ............... 73/1.86 |
| 2004/0127815 A1 | 7/2004 | Marchitto et al. |
| 2004/0138563 A1 | 7/2004 | Moehring et al. |
| 2004/0236248 A1 | 11/2004 | Svedman |
| 2004/0243021 A1 | 12/2004 | Murphy et al. |
| 2005/0038339 A1 | 2/2005 | Chauhan et al. |
| 2005/0154314 A1 | 7/2005 | Quistgaard |
| 2005/0283098 A1* | 12/2005 | Conston et al. ............... 601/2 |
| 2006/0060991 A1 | 3/2006 | Holsteyns et al. |
| 2006/0074303 A1 | 4/2006 | Chornenky et al. |
| 2006/0206028 A1 | 9/2006 | Lee et al. |
| 2006/0241466 A1* | 10/2006 | Ottoboni et al. ............... 600/458 |
| 2006/0241523 A1 | 10/2006 | Sinelnikov et al. |
| 2006/0264760 A1 | 11/2006 | Liu et al. |
| 2007/0010805 A1 | 1/2007 | Fedewa et al. |
| 2007/0016039 A1 | 1/2007 | Vortman et al. |
| 2007/0065420 A1 | 3/2007 | Johnson |
| 2007/0083120 A1 | 4/2007 | Cain et al. |
| 2007/0161902 A1 | 7/2007 | Dan |
| 2007/0219448 A1 | 9/2007 | Seip et al. |
| 2008/0013593 A1* | 1/2008 | Kawabata ............... 374/17 |
| 2008/0082026 A1 | 4/2008 | Schmidt et al. |
| 2008/0126665 A1 | 5/2008 | Burr et al. |
| 2008/0214964 A1 | 9/2008 | Chapelon et al. |
| 2008/0262345 A1 | 10/2008 | Fichtinger et al. |
| 2008/0262486 A1 | 10/2008 | Zvuloni et al. |
| 2008/0312561 A1 | 12/2008 | Chauhan |
| 2008/0319356 A1 | 12/2008 | Cain et al. |
| 2009/0030339 A1 | 1/2009 | Cheng et al. |
| 2009/0112098 A1 | 4/2009 | Vaezy et al. |
| 2009/0177085 A1 | 7/2009 | Maxwell et al. |
| 2009/0198094 A1 | 8/2009 | Fenster et al. |
| 2009/0211587 A1 | 8/2009 | Lawrentschuk |
| 2009/0227874 A1 | 9/2009 | Suri et al. |
| 2010/0069797 A1 | 3/2010 | Cain et al. |
| 2010/0125225 A1 | 5/2010 | Gelbart et al. |
| 2010/0286519 A1 | 11/2010 | Lee et al. |
| 2010/0317971 A1 | 12/2010 | Fan et al. |
| 2011/0040190 A1 | 2/2011 | Jahnke et al. |
| 2011/0172529 A1 | 7/2011 | Gertner |
| 2012/0010541 A1 | 1/2012 | Cain et al. |
| 2012/0029353 A1 | 2/2012 | Slayton et al. |
| 2012/0092724 A1 | 4/2012 | Pettis |
| 2012/0130288 A1* | 5/2012 | Holland et al. ............... 601/2 |
| 2012/0189998 A1* | 7/2012 | Kruecker et al. ............... 434/272 |
| 2012/0271167 A1* | 10/2012 | Holland et al. ............... 600/439 |
| 2013/0053691 A1* | 2/2013 | Kawabata et al. ............... 600/431 |

FOREIGN PATENT DOCUMENTS

| | | |
|---|---|---|
| EP | 0017382 A1 | 10/1980 |
| EP | 0320303 A2 | 6/1989 |
| EP | 0332871 A2 | 9/1989 |
| EP | 0384831 A2 | 8/1990 |
| EP | 0755653 A1 | 1/1997 |
| GB | 2099582 A | 12/1982 |
| JP | 2010029650 A * | 2/2010 |
| WO | WO94/06355 A1 | 3/1994 |
| WO | WO 02/32506 A1 | 4/2002 |

OTHER PUBLICATIONS

Cain, Charles A.; Histrotripsy: controlled mechanical sub-division of soft tissues by high intensity pulsed ultrasound (conference presentation); American Institute of Physics (AIP) Therapeutic Ultrasound: 5th International Symposium on Therapeutic Ultrasound; 44 pgs.; Oct. 27-29, 2005.

Parsons et al.; Pulsed cavitational ultrasound therapy for controlled tissue homogenization; Ultrasound in Med. & Biol.; vol. 32; pp. 115-129; 2006.

Roberts et al.; Pulsed cavitational ultrasound: a noninvasive technology for controlled tissue ablation (histotripsy) in the rabbit kidney; Journal of Urology; vol. 175; pp. 734-738; 2006.

Xu et al.; A new strategy to enhance cavitational tissue erosion by using a high intensity initiating sequence; IEEE Trans Ultrasonics Ferroelectrics and Freq Control; vol. 53; pp. 1412-1424; 2006.

Xu et al.; Controlled ultrasound tissue erosion: the role of dynamic interaction between insonation and microbubble activity; Journal of the Acoustical Society of America; vol. 117; pp. 424-435; 2005.

Xu et al.; Controlled ultrasound tissue erosion; IEEE Transaction on Ultrasonics, Ferroelectrics, and Frequency Control; vol. 51; pp. 726-736; 2004.

Xu et al.; Effects of acoustic parameters on bubble cloud dynamics in ultrasound tissue erosion (histotripsy); Journal of the Acoustical Society of America; vol. 122; pp. 229-236; 2007.

Xu et al.; High Speed Imaging of Bubble Clouds Generated in Pulsed Ultrasound Cavitational Therapy Histotripsy; IEEE Trans Ultrason Ferroelectr Freq Control; ; vol. 54; No. 10; pp. 2091R2101; Oct. 2007.

Xu et al.; Investigation of intensity threshold for ultrasound tissue erosion; Ultrasound in Med. & Biol.; vol. 31; pp. 1673-1682; 2005.

Xu et al.; Optical and acoustic monitoring of bubble cloud dynamics at a tissue-fluid interface in ultrasound tissue erosion; Journal of the Acoustical Society of America; vol. 121; pp. 2421-2430; 2007.

Hall et al.; U.S. Appl. No. 12/868,768 entitled "Micromanipulator Control Arm for Therapeutic and Imaging Ultrasound Transducers," filed Aug. 26, 2010.

Cain et al.; U.S. Appl. No. 12/868,775 entitled "Devices and Methods for Using Controlled Bubble Cloud Cavitation in Fractionating Urinary Stones," filed Aug. 26, 2010.

Appel et al.; Stereoscopic highspeed recording of bubble filaments; Ultrasonics Sonochemistry; vol. 11(1); pp. 39-42; Jan. 2004.

Atchley et al.; Thresholds for cavitation produced in water by pulsed ultrasound; Ultrasonics.; vol. 26(5); pp. 280-285; Sep. 1988.

Bland et al.; Surgical Oncology; McGraw Hill; Chap. 5 (Cavitron Ultrasonic Aspirator); pp. 461-462; Jan. 29, 2001.

Burdin et al.; Implementation of the laser diffraction technique for cavitation bubble investigations; Particle & Particle Systems Characterization; vol. 19; pp. 73-83; May 2002.

Holland et al.; Thresholds for transient cavitation produced by pulsed ultrasound in a controlled nuclei environment; J. Acoust. Soc. Am.; vol. 88(5); pp. 2059-2069; Nov. 1990.

Huber et al.; Influence of shock wave pressure amplitude and pulse repetition frequency on the lifespan, size and number of transient cavities in the field of an electromagnetic lithotripter; Physics in Medicine and Biology; vol. 43 (10); pp. 3113-3128; Oct. 1998.

Lauterborn et al.; Cavitation bubble dynamics studied by high speed photography and holography: part one; Ultrasonics; vol. 23; pp. 260-268; Nov. 1985.

Miller et al.; A review of in vitro bioeffects of inertial ultrasonic cavitation from a mechanistic perspective; Ultrasound in Medicine and Biology; vol. 22; pp. 1131-1154; (year of publication is sufficiently earlier than the effective U.S. filing date and any foreign priority date) 1996.

Ohl et al.; Bubble dynamics, shock waves and sonoluminescence; Phil. Trans. R. Soc. Lond. A; vol. 357; pp. 269-294; (year of publication is sufficiently earlier than the effective U.S. filing date and any foreign priority date) 1999.

Pishchalnikov et al.; Cavitation Bubble Cluster Activity in the Breakage of Kidney Stones by Lithotripter Shock Waves; J Endourol.; 17(7): 435-446; Sep. 2003.

Porter et al.; Reduction in left ventricular cavitary attenuation and improvement in posterior myocardial contrast . . . ; J Am Soc Echocardiography; pp. 437-441; Jul.-Aug. 1996.

Roy et al.; A precise technique for the measurement of acoustic cavitation thresholds and some preliminary results; Journal of the Acoustical Society of America; vol. 78(5); pp. 1799-1805; Nov. 1985.

Sapozhnikov et al.; Ultrasound-Guided Localized Detection of Cavitation During Lithotripsy in Pig Kidney in Vivo; IEEE Ultrasonics Symposium, vol. 2; pp. 1347-1350; Oct. 7-10, 2001.

Sokolov et al.; Use of a dual-pulse lithotripter to generate a localized and intensified cavitation field; Journal of the Acoustical Society of America; vol. 110(3); pp. 1685-1695; Sep. 2001.

Teofilovic, Dejan; U.S. Appl. No. 13/446,783 entitled "Systems and Methods for Obtaining Large Creepage Isolation on Printed Circuit Boards," filed Apr. 13, 2012.

Cain, Charles A.; U.S. Appl. No. 13/570,708 entitled "Lesion Generation Through Bone Using Histotripsy Therapy Without Aberration Correction," filed Aug. 9, 2012.

Cain et al.; U.S. Appl. No. 13/648,955 entitled "Pulsed Cavitational Therapeutic Ultrasound With Dithering," filed Oct. 10, 2012.

Cain et al.; U.S. Appl. No. 13/648,965 entitled "Imaging Feedback of Histotripsy Treatments with Ultrasound Transient Elastography," filed Oct. 10, 2012.

Avago Technologies; ACNV2601 High Insulation Voltage 10 MBd Digital Opotcoupler. Avago Technologies Data Sheet; pp. 1-11; Jul. 29, 2010.

* cited by examiner

GEL PHANTOMS FOR TESTING CAVITATIONAL ULTRASOUND (HISTOTRIPSY) TRANSDUCERS

CROSS REFERENCE TO RELATED APPLICATIONS

This application claims the benefit under 35 U.S.C. 119 of U.S. Provisional Patent Application No. 61/244,619, filed Sep. 22, 2009, titled "Gel Phantoms for Testing Cavitational Ultrasound (Histotripsy) Transducers". This application is herein incorporated by reference in its entirety.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD OF THE INVENTION

The present invention generally relates to cavitational ultrasound therapy (e.g., Histotripsy). More specifically, the present invention relates to testing cavitational ultrasound transducers with gel phantoms.

BACKGROUND OF THE INVENTION

Histotripsy is a non-invasive tissue ablation modality that focuses pulsed ultrasound from outside the body to a target tissue inside the body. Histotripsy mechanically damages tissue through cavitation of microbubbles.

Histotripsy is the mechanical disruption via acoustic cavitation of a target tissue volume or tissue embedded inclusion as part of a surgical or other therapeutic procedure. Histotripsy works best when a whole set of acoustic and transducer scan parameters controlling the spatial extent of periodic cavitation events are within a rather narrow range. Small changes in any of the parameters can result in discontinuation of the ongoing process.

Histotripsy is a new therapy modality and no methods currently exist to give an immediate indication of the spatial extent of tissue disruption. A range or workable parameters can be determined in the lab using in vitro and in vivo tissue disruption experiments with subsequent histological examination of the targeted tissue. This process can be time-consuming as histological slides take hours to days to process and read. While such experiments are necessary before clinical application, a quick "indicator" approach as a rapid check on system performance would be highly useful, particularly when a new optimized parameter set for particular clinical application is being designed.

SUMMARY OF THE INVENTION

In some embodiments, a cavitational damage indicator phantom is provided comprising a container, a gel disposed in the container, and an indicator disposed in the container, the indicator configured to change visibly during application of cavitational ultrasound energy to the indicator.

In some embodiments, the indicator is embedded between first and second layers of the gel. In other embodiments, the indicator comprises a layer having a thickness of less than 5 mm. In some embodiments, the gel comprises an agarose gel. In some embodiments, the indicator comprises a plurality of layers disposed in the container or in the gel. In additional embodiments, the indicator comprises a plurality of carbon particles. In some embodiments, the indicator comprises a plurality of microspheres. The microspheres can comprise polystyrene beads, or microencapsulated beads, for example. In one embodiment, the indicator comprises red blood cells.

In some embodiments, the visible change of the indicator can be detected by a human eye. In some embodiments, the visible change comprises the carbon particles becoming darker during application of cavitational ultrasound energy to the indicator. In additional embodiments, the visible change comprises a breakdown of the size of the carbon particles. In another embodiment, the visible change comprises spilling a pigment from the microspheres during application of cavitational ultrasound energy to the indicator.

In one embodiment, the container is at least partially transparent. In another embodiment, the gel is transparent or translucent.

A cavitational damage testing system is provided, comprising a tank filled with an acoustic medium, and a cavitational ultrasound phantom disposed in the tank, the cavitational ultrasound phantom comprising a container, a gel disposed in the container, and an indicator disposed in the container, the indicator configured to change visibly under application of cavitational ultrasound energy to the indicator.

In some embodiments, the indicator is embedded between first and second layers of the gel. In other embodiments, the indicator comprises a layer having a thickness <5 mm. In one embodiment, the gel comprises a transparent agarose gel.

In some embodiments, the indicator comprises a plurality of carbon particles. In other embodiments, the indicator comprises a plurality of microspheres. The microspheres can comprise polystyrene beads or microencapsulated beads. In another embodiment, the indicator comprises red blood cells.

In some embodiments, the cavitational damage testing system further comprises a mount disposed on or near the tank, the mount configured to receive a cavitational ultrasound transducer. In one embodiment, the mount is configured to align a focal point of the cavitational ultrasound transducer with the cavitational ultrasound phantom.

In one embodiment, the cavitational damage testing system further comprises a cavitational ultrasound therapy transducer configured to deliver cavitational ultrasound energy to the cavitational ultrasound phantom.

In another embodiment, the cavitational damage testing system further comprises an imaging system. The imaging system can be a high-speed video camera or an ultrasound imaging system, for example.

In some embodiments, the acoustic medium comprises degassed water.

A method of testing a Histotripsy transducer is provided, comprising applying Histotripsy energy to a Histotripsy phantom, and observing a visual change in the Histotripsy phantom.

In some embodiments, the visual change comprises a color change.

In another embodiment, the Histotripsy phantom comprises carbon particles disposed in a transparent gel and the visual change comprises observing the carbon particles change to a darker color.

In one embodiment, the Histotripsy phantom comprises microspheres disposed in a transparent gel and the visual change comprises releasing a dye from the microspheres during application of Histotripsy energy to the Histotripsy phantom.

In another embodiment, the method comprises, prior to the applying step, placing the Histotripsy phantom in a testing tank, and aligning a focal point of a Histotripsy transducer with the Histotripsy phantom.

In some embodiments, the applying Histotripsy energy step comprises applying Histotripsy energy to the Histotripsy phantom with the Histotripsy transducer.

In some embodiments, the Histotripsy phantom resembles a human prostate. In another embodiment, the visual change observed in the Histotripsy phantom is indicative of tissue damage to be expected during a Histotripsy procedure in a human patient.

DETAILED DESCRIPTION OF THE INVENTION

Several novel methods, procedures, and devices for quick and inexpensive testing of cavitational ultrasound (e.g., such as Histotripsy) transducers are disclosed herein. The devices and methods can also allow preliminary testing of new acoustic parameter or acoustic scanning algorithms without the use of in vivo or excised tissues with subsequent histological studies, and without the need for tedious and time consuming hydrophone field pattern scanning.

The devices and methods described herein can also allow instantaneous verification of the efficacy of transducer and/or acoustic parameter sets, either via plain sight observation or microscopic observation prior to clinical application. The methods involve fabrication of optically transparent gels with indicator inclusions that are affected by incident Histotripsy ultrasound in a way that usefully mimics tissue damage to give immediate visual feedback of the volume and degree of damage produced. The indicator(s) can show up as a change in color or transparency produced by cavitation of the kind that produces tissue disruption or mechanical fractionation. Since the methods and devices described herein allow instant visual feedback, they can also be a useful research tool.

A useful indicator device, which may be referred to henceforth as a "phantom," can be fabricated by embedding materials, agents, reagents, extracted cells, or processed tissue extracts (or fragments) in a transparent gel, which can be affected or changed immediately in some visible way by application of cavitational ultrasound (e.g., Histotripsy) energy to the indicator. Because the phantoms can be easily used and give immediate results under plain sight observation, these phantoms can be packaged and preserved for long shelf life to be used with Histotripsy systems.

The methods described herein can also be used to check on efficacy of acoustic parameter changes, and for testing new transducer spatial/temporal scan patterns and parameters. These methods lend themselves to rapid verification, even in the clinic, of the spatial extent of tissue damage expected for a given set of acoustic and scan parameters. Such indicator devices or phantoms can be useful adjuncts to commercially available Histotripsy systems and may be used as consumable products by those who have purchased Histotripsy systems.

By using the parameters intended for therapeutic application, a user can see in real time, or immediately after an exposure paradigm, the spatial extent and degree of tissue disruption that might be expected during the actual treatment. This can be seen visually (by the unaided eye), by a color change or transparency change of an indicator in the phantom that would indicate the volume extent of a lesion expected in the therapeutic application. A photographic or microscopic record can also be produced for further assessment at much higher resolution. Photographic or microscopic devices can be included with some embodiments of Histotripsy testing systems described herein.

The substrate for a viable indicator phantom can be a transparent gel consisting of an aqueous solution of a gelling agent (e.g., agarose, acrylamide, etc.) into which is placed an indicator which can be disrupted or changed in some way by cavitating histotripsy pulses. The change produces a color change in the affected volume showing through the transparent phantom exactly the volume affected by the transducer (with appropriate acoustic and scan parameter set) chosen for testing. Gel design can include such important parameters as melting temperature, optical transparency, hardness, mechanical stability, and shelf life of the product.

Figure 1:
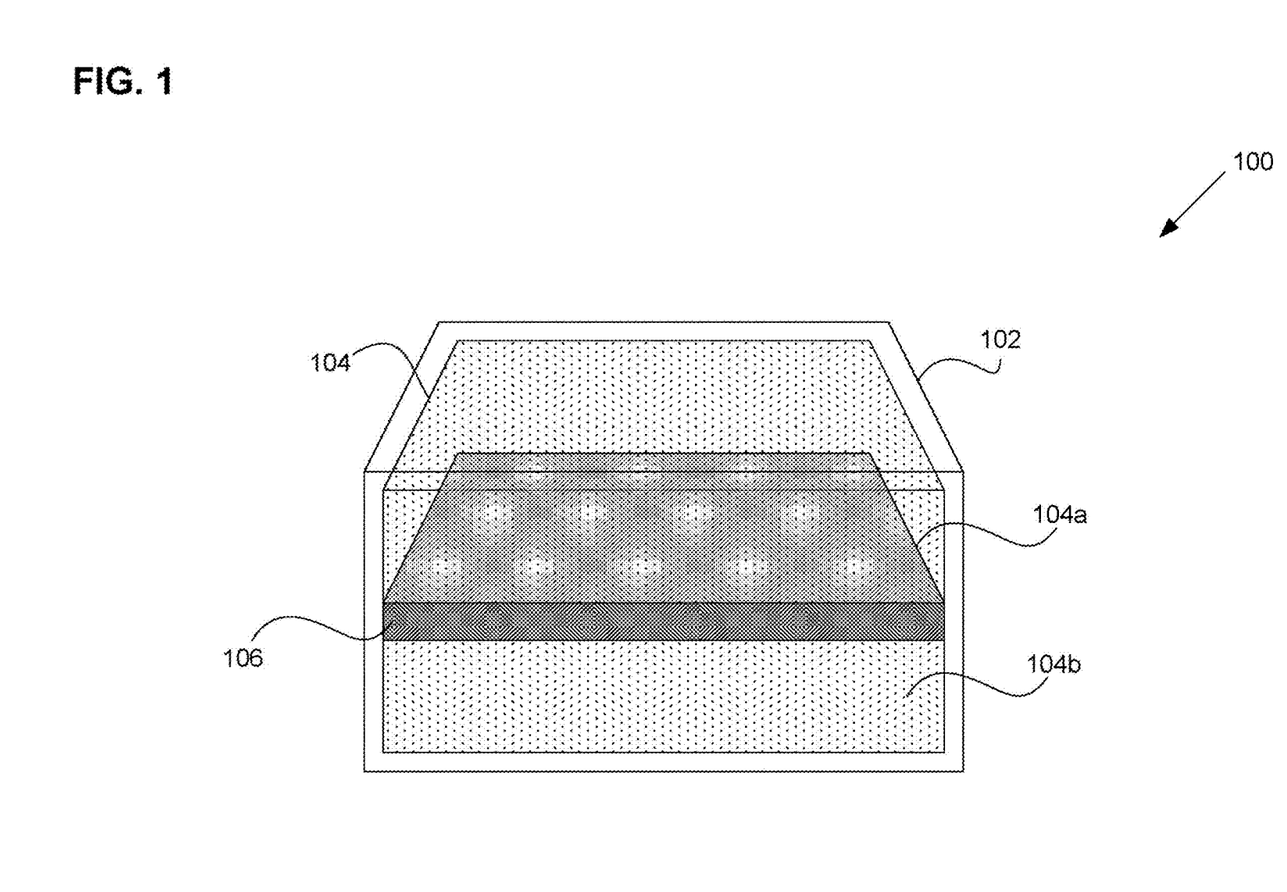
FIG. 1 illustrates one embodiment of a Histotripsy phantom.

Referring now to the drawings, FIG. 1 illustrates a Histotripsy phantom 100 comprising a container 102, a gel 104 disposed in the container, and an indicator 106 disposed in the container. Although the phantom 100 is described as a Histotripsy phantom, it should be understood that the phantom can be used with any form of cavitational ultrasound. As shown in FIG. 1, the gel 104 can comprise two layers 104a and 104b, with the indicator 106 sandwiched between the two gel layers. The indicator layer can have a thickness of less than 5 mm, for example, and the gel layers can have any desired thickness depending on the size of the container. In some embodiments, the gel is transparent to allow direct visualization of the indicator through the gel. In other embodiments, the gel is translucent, which still allows for direct visualization of the indicator through the gel. The gel can be an agarose gel, for example, which provides for a transparent and acoustically transmissive medium. In some embodiments, either the entire container or at least a portion of the container (e.g., the top of the container) is transparent or translucent to allow for direct visualization of the indicator through both the gel and the container.

The indicator can be cast into the gel in different geometries, e.g., in thin sheets or planes at high concentration with very transparent layers on top and bottom. Such a construct would allow a cross-section to be seen very clearly with boundary effects clearly assessed with just a glance or in more detail by macro-photography or microscopy. Multiple layers of indicators within the gel can allow such assessments to be made in different planes. Or, a whole volume-effect can be discerned if the indicator is distributed uniformly throughout the gel and container. Indicator shapes mimicking target volumes can also be cast in the container, allowing for practice phantoms useful in finding optimized histotripsy parameter sets. For example, an indicator can have the shape of a prostate. In some embodiments, scatterers can be added to the phantom to make the acoustic properties of the gel similar to soft tissue, including impedance and attenuation. The containers can also include skeletal models embedded in the gel (e.g., a skeletal model of the pelvis in the prostate indicator embodiment) designed to mimic ultrasound attenuation of surrounding bone and tissues.

Other variations are possible including gel phantoms with a monolayer of cells grown on a surface for surface erosion studies, or a monolayer grown on a surface overfilled with another transparent volume. This can be used to study the effects of Histotripsy on a layer of cells, perhaps producing a diffusion resistant barrier, useful for testing drug delivery modes for Histotripsy.

The indicator 106 can be configured to change visually during application of cavitational ultrasound (e.g., Histotripsy) energy to the indicator. The visual change of the indicator can be, for example, a color change (e.g., a change from white to red), a change in darkness (e.g., a change from light to dark or from dark to light), or a change in transparency (e.g., from transparent to translucent or opaque).

Figure 2:
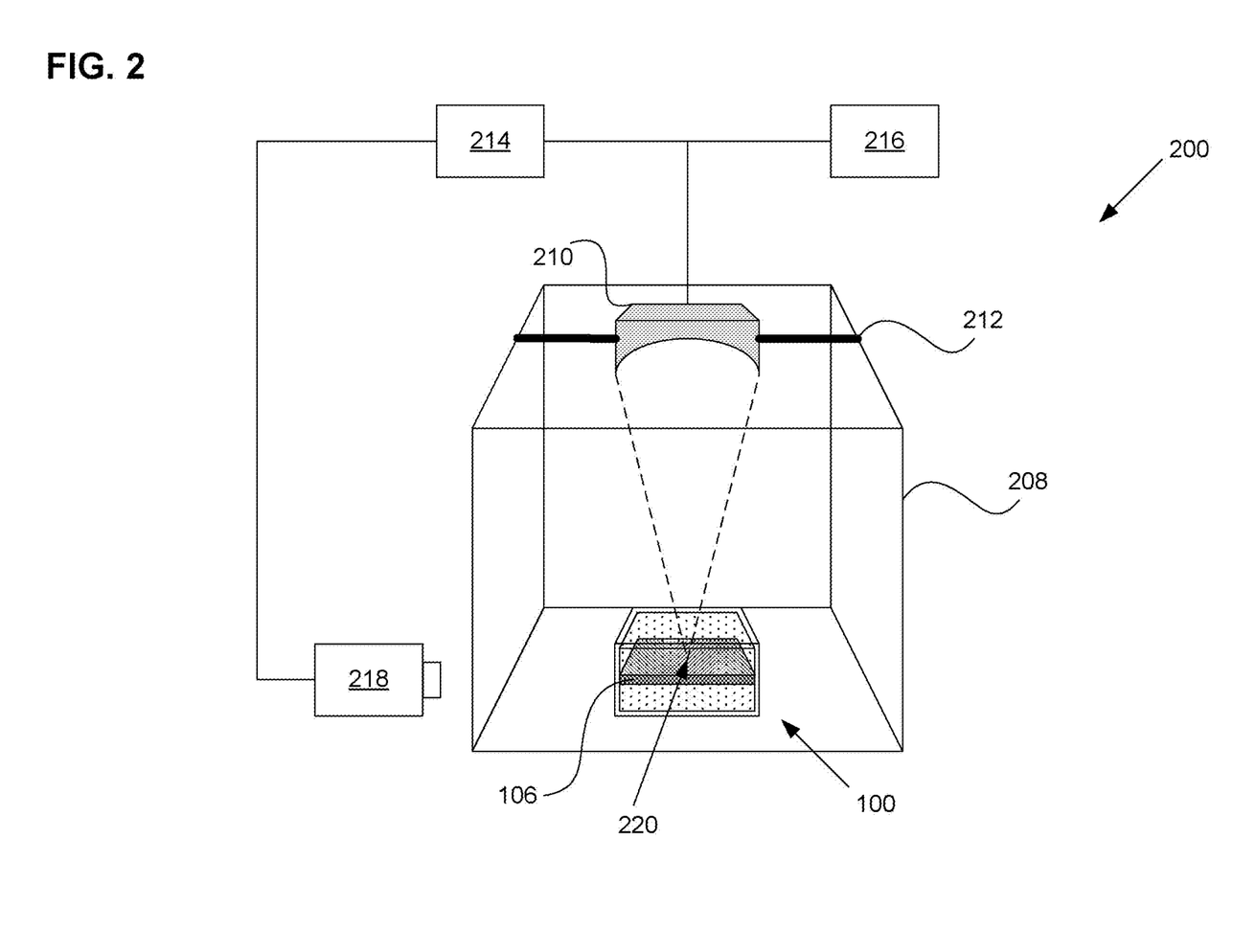
FIG. 2 illustrates one embodiment of a Histotripsy testing system.

FIG. 2 illustrates a Histotripsy testing system 200 comprising a Histotripsy phantom 100 (such as Histotripsy phantom 100 from FIG. 1), tank 208, Histotripsy transducer 210, mount 212, controller 214, RF amplifier 216, and imaging system 218. The tank can be filled with an acoustic coupling medium, such as degassed water for example. Controller 214 and RF amplifier 216 can be configured to drive Histotripsy transducer 210 to deliver cavitational ultrasound (e.g., Histotripsy) energy to a target. In some embodiments, the controller, RF amplifier, and Histotripsy transducer are configured to apply cavitational ultrasound (e.g., Histotripsy) energy comprising acoustic pulses that operate at a frequency between approximately 50 KHz and 5 MHz, having a pulse intensity with a peak negative pressure of approximately 8-40 MPa, a peak positive pressure of more than 10 MPa, a pulse length shorter than 50 cycles, a duty cycle of less than 5%, and a pulse repetition frequency of less than 5 KHz. These Histotripsy parameters are sufficient to allow for the generation of cavitational microbubbles in a target (such as the indicator phantom).

The tank can further include a mount configured to receive the Histotripsy transducer 210. In some embodiments, the mount is moveable to allow for alignment of focal point 220 of the Histotripsy transducer with the Histotripsy phantom, and more particularly, with the indicator 106 of the phantom. In other embodiments, the phantom itself can be mounted to a moveable mount, such as a mechanical arm, and the position of the transducer on the tank is fixed. In this embodiment, the phantom can be moved to align a focal point 220 of the transducer with the indicator of the phantom.

The Histotripsy testing system can also include an imaging system 218 to allow for photographic, microscopic, ultrasound, and/or video imaging of the phantom prior to, during, and after application of cavitational ultrasound (e.g., Histotripsy) energy. The imaging system can comprise a still camera, a video camera, an ultrasound imaging probe, and/or a microscope, for example.

Many types of indicators can be used in phantom 100 and system 200 of FIGS. 1-2. Referring back to FIG. 1, in one embodiment, the indicator 106 can comprise a plurality of carbon particles, such as graphite powder. In some embodiments, the aggregate size of the graphite powder particles can be approximately 100-200 μm and the carbon particles indicator layer can be a 0.25% w/v of graphite powder to agarose solution, for example. This particular ratio may allow for a degree of translucency which is important for the direct visualization of Histotripsy lesions.

Figure 3A:
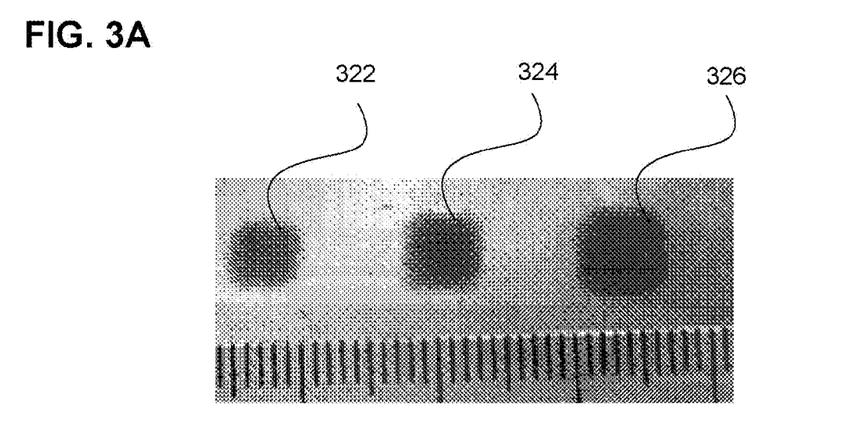
FIGS. 3A-3B illustrate a plain eye view and a microscopic view, respectively, of a carbon particle gel phantom after application of Histotripsy energy.
Figure 3B:
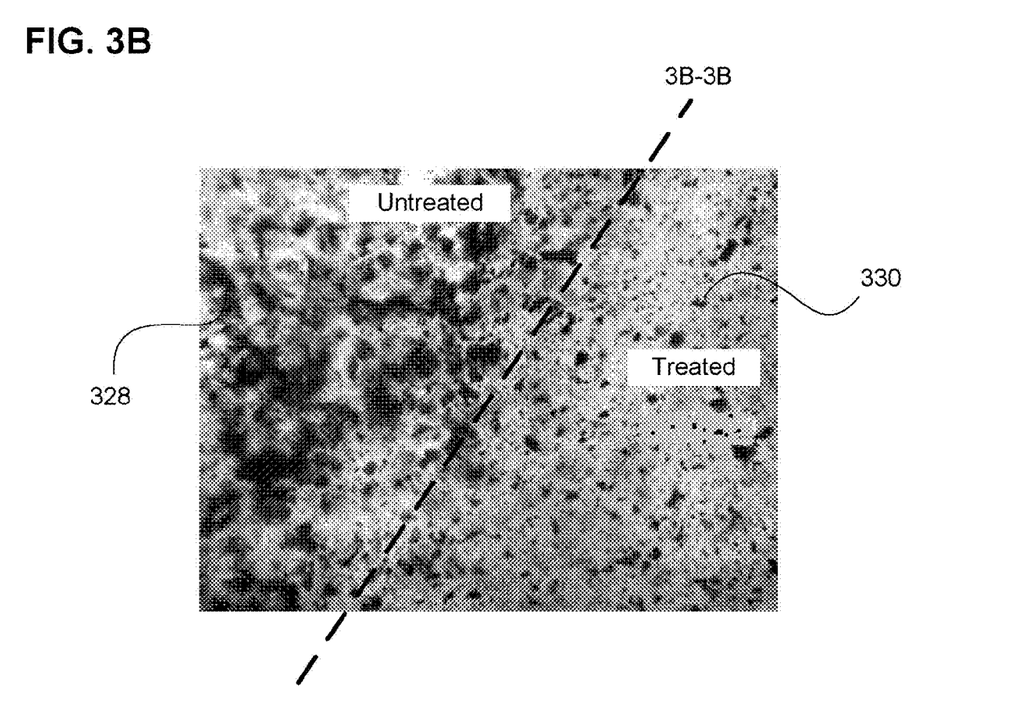

FIGS. 3A-3B illustrate a top down plain eye view and a microscopic view, respectively, of a gel phantom with a carbon particle indicator after application of cavitational ultrasound (e.g., Histotripsy) energy. As shown in FIG. 3A, lesions 322, 324, and 326 can be clearly seen with the naked eye as dark spots or regions which are surrounded by lighter, untreated regions in the carbon particle indicator. Application of cavitational ultrasound (e.g., Histotripsy) energy to the carbon particle indicator mechanically breaks down the carbon particles, which can cause the color of the indicator to change visibly to the naked eye from a light shade to a dark shade. Additionally, direct visualization of the phantom can also show dose dependency. For example, still referring to FIG. 3A it can be seen that lesion 322 received a lower dose of Histotripsy than lesion 324, which received a lower dose of Histotripsy than lesion 326. Lesion 322 is the lightest of the three lesions, and shows the least defined borders. In contrast, lesion 326 is much darker than lesions 322 and 324, and also has cleaner, more defined borders. In one embodiment, lesions 322, 324, and 326 represent application of 2000, 4000, and 6000 Histotripsy pulses to the carbon particle indicator, respectively.

FIG. 3B illustrates a microscopic view of the carbon particle indicator before and after application of Histotripsy therapy. As shown, the untreated carbon particles 328 on the left of line 3B-3B are larger than the treated carbon particles 330 on the right of line 3B-3B. Prior to treatment, carbon aggregate size may range upwards of 100-200 μm. After application of cavitational ultrasound (e.g., Histotripsy) energy, the carbon particles can have a size smaller than 20 μm, depending on the Histotripsy dose. Thus, the change in aggregate size of carbon particles before and after cavitational ultrasound (e.g., Histotripsy) energy delivery can easily be seen with a microscope in addition to the naked eye.

Referring back to FIG. 1, in another embodiment, the indicator 106 can comprise a plurality of microencapsulated dye beads. In some embodiments, the aggregate size of the microencapsulated dye beads can be approximately 75-100 μm in diameter that encapsulate <5 μm pigments. The dye can be encapsulated in any thin shell (constructed of a polymer, protein, lipid, etc.) In one embodiment, the dye bead indicator layer can be 8% w/v of dye beads to agarose solution, for example. This particular ratio may allow for a degree of translucency which is important for the direct visualization of Histotripsy lesions.

Figure 4A:
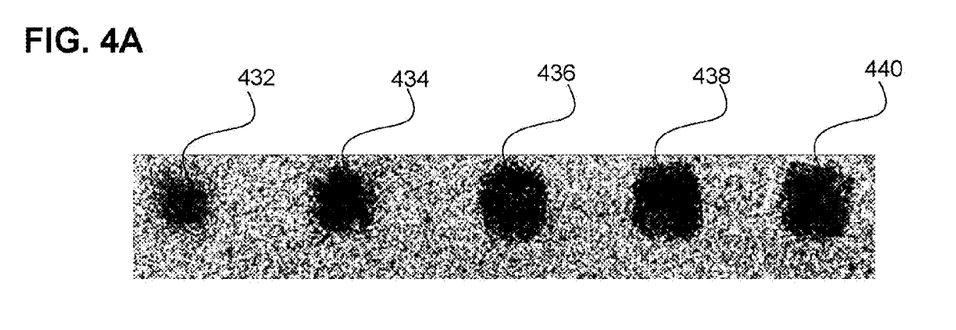
FIGS. 4A-4B illustrate a plain eye view and a microscopic view, respectively, of a microencapsulated dye bead gel phantom after application of Histotripsy energy.
Figure 4B:
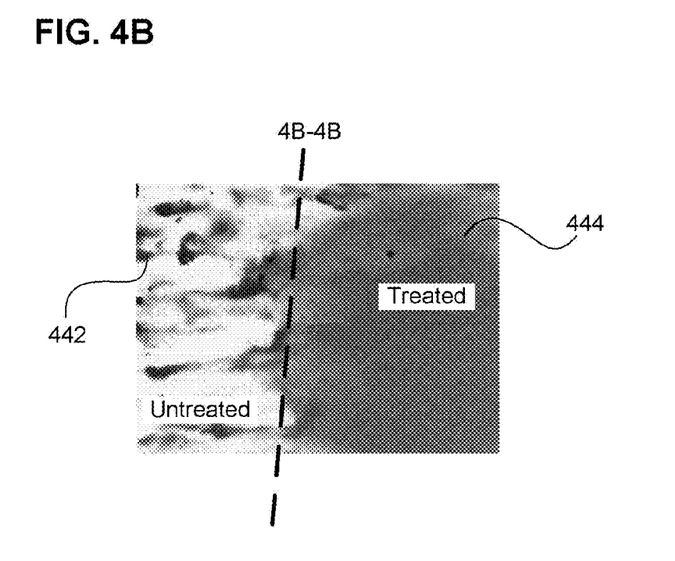

FIGS. 4A-4B illustrate a top down plain eye view and a microscopic view, respectively, of a gel phantom with a microencapsulated dye beads indicator after application of cavitational ultrasound (e.g., Histotripsy) energy. As shown in FIG. 4A, lesions 432, 434, 436, 438, and 440 can be clearly seen with the naked eye as colored spots or regions which are surrounded by transparent/translucent, untreated regions in the dye bead indicator. Although the illustrations are shown in black and white, it should be understood that the dye encapsulated in the beads can be any color (e.g., red, blue, black, etc). Ideally, the color of the dye can be easily distinguished from Application of cavitational ultrasound (e.g., Histotripsy) energy to the dye bead indicator can mechanically fractionate the dye beads, releasing the colored dye into the phantom so that it is visible to the naked eye. Additionally, direct visualization of the phantom can also show dose dependency, although not to the extent that can be seen with the carbon particle indicator. For example, still referring to FIG. 4A it can be seen that lesion 432 received a lower dose of Histotripsy than lesions 434, 436, and 438, which received a lower dose of Histotripsy than lesion 440. Lesion 432 is the smallest and least defined of the five lesions. In contrast, lesion 440 is much darker than the other lesions, and also has cleaner, more defined borders. In one embodiment, lesions 432, 434, 436, 438, and 440 represent application of 500, 1000, 2000, 4000, and 6000 Histotripsy pulses to the microencapsulated dye beads indicator, respectively.

FIG. 4B illustrates a microscopic view of the microencapsulated dye beads indicator before and after application of Histotripsy therapy. As shown, the untreated beads 442 on the left of line 4B-4B can be distinguished from released dye 444 on the right of line 4B-4B. Prior to treatment, the dye beads may have a size of approximately 75-100 µm. After application of cavitational ultrasound (e.g., Histotripsy) energy, the beads are destroyed allowing the dye to spill into the surrounding gel phantom. Thus, the release of dye from the microencapsulated beads after cavitational ultrasound (e.g., Histotripsy) energy delivery can easily be seen with a microscope in addition to the naked eye.

Referring again to FIG. 1, in another embodiment, the indicator 106 can comprise a plurality of leuco dye beads. Leuco dye beads can include an interior dye, which upon release, chemically combine with a separate indicator powder to change colors. In some embodiments, the leuco dye beads can be approximately 5-10 µm in diameter. In one embodiment, the leuco dye bead indicator layer can be 20% w/v of leuco dye beads to agarose solution, for example. Any ratio of beads to indicator powder can be used, but in some embodiments, a 2:1 ratio of beads to indicator powder shows the highest intensity of color change.

In some embodiments of the dye beads, the dye can be a fluorescent dye which is quenched either in the encapsulated or un-encapsulated state, thus producing a clear or fluorescent volume when the enclosing capsules are disrupted by Histotripsy cavitation. This embodiment may require subsequent exposure to an excitation illumination for assay after the test procedure, most likely with ultraviolet light.

In yet another embodiment, the indicator can be a dye or fluorescent dye conjugated with the gel producing a material which cannot diffuse freely in the gel, which might then be exposed to Histotripsy sequences. The resulting cavitation can produce free radicals (e.g., active oxygen species, or hydroxyl radicals) all of which may bleach or chemically modify the indicator dye changing (or removing) its color or fluorescent activity. In any case, such modification would produce a volume easily seen as that which is affected by the cavitation activity.

Figure 5A:
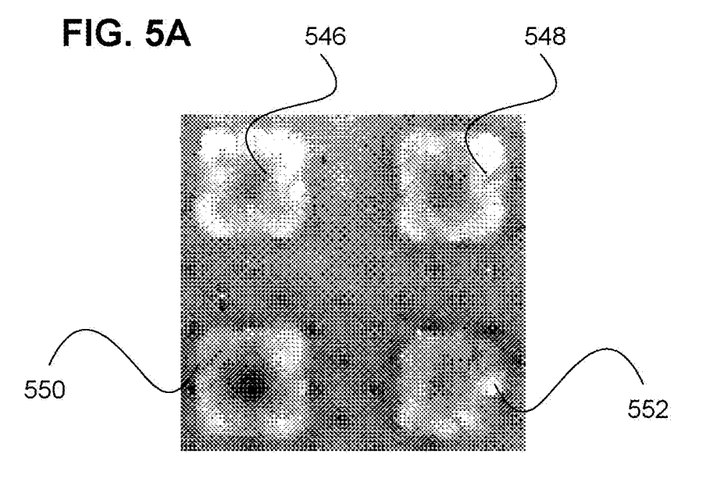
FIGS. 5A-5B illustrate a plain eye view and a microscopic view, respectively, of a Leuco dye-encapsulated bead gel phantom after application of Histotripsy energy.
Figure 5B:
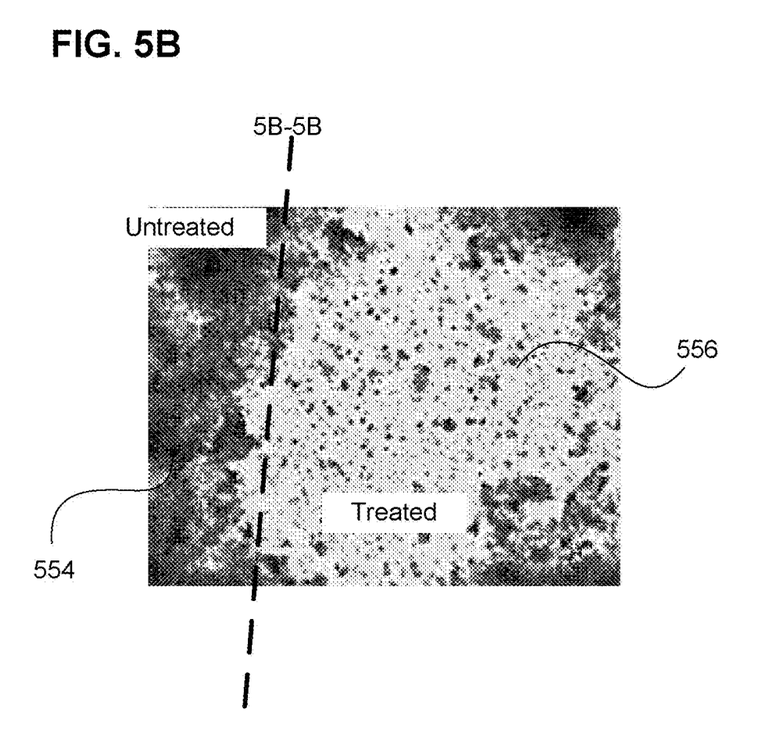

FIGS. 5A-5B illustrate a top down plain eye view and a microscopic view, respectively, of a gel phantom with a leuco dye beads indicator after application of cavitational ultrasound (e.g., Histotripsy) energy. As shown in FIG. 5A, lesions 546, 548, 550, and 552 can be clearly seen with the naked eye as colored spots or regions which are surrounded by transparent/translucent, untreated regions in the dye bead indicator. Application of cavitational ultrasound (e.g., Histotripsy) energy to the dye bead indicator can mechanically fractionate the dye beads, releasing the dye into the phantom which chemically reacts with the indicator powder, causing a color change that it is visible to the naked eye. The lesions in the phantom can be seen as "donuts" with clearly defined boundaries and a dark gray interior region. Additionally, direct visualization of the phantom can also show dose dependency, although not to the extent that can be seen with the carbon particle indicator.

FIG. 5B illustrates a microscopic view of the leuco dye beads indicator before and after application of Histotripsy therapy. As shown, the untreated dye beads 554 on the left of line 5B-5B can be distinguished from the chemically reacted dye 556 on the right of line 5B-5B. Prior to treatment, the dye beads may have a size of approximately 5-10 µm. After application of cavitational ultrasound (e.g., Histotripsy) energy, the beads are destroyed allowing the dye to spill into the surrounding gel phantom to react with the indicator powder. Thus, the release of dye from the microencapsulated beads after cavitational ultrasound (e.g., Histotripsy) energy delivery can easily be seen with a microscope in addition to the naked eye.

Although not shown in the drawings, an alternate embodiment of an indicator can comprise polystyrene beads. The polystyrene beads can show a visual change between treated and untreated portions. However, since the polystyrene beads are semi-translucent, they can be more difficult to differentiate against the gel layers than the other embodiments described above.

In an additional embodiment the indicator 106 can comprise red blood cells. Application of cavitational ultrasound (e.g., Histotripsy) energy to a gel phantom having a red blood cell indicator can create changes to the indicator visible to the naked eye, as described above in the other embodiments. Histotripsy pulses, if adjusted for tissue disruption, will break up the red blood cells in a manner very similar to disruption of living tissue with the same boundary between affected and non affected tissue. When the red blood cells are disrupted, the gel is rendered clear (no pink color) in the disrupted volume clearly showing at one glance the spatial extent of the disrupted volume. This volume can show the extent of the cavitation activity and, therefore, the expected damage zone to be produced clinically. Therefore, a very quick visual test of the transducer can be possible immediately before treatment. Moreover, the boundary can be assessed by macro photography, or microscopy, to see boundary effects more clearly.

In other embodiments, gels with temperature indicators as well as cavitation indicators can be used for assessing possible thermal complications of certain (e.g., high PRF) parameters.

It is also important to note that the phantom can be engineered to give both visual (it is a transparent gel with specially formulated inclusions) as well as the same ultrasound imaging feedback as real tissue for different histotripsy dose. Thus one could fabricate a clear gel phantom which would look under ultrasound imaging just like the real tissue to be treated, (e.g., the prostate, uterine fibroid, breast cancer, etc.) Then, one could see instantly with the eye or ultrasound imaging how any new parameter set or focus scanning paradigm would likely work in vivo. Lesions in the phantoms show reduced echogenecity in B-mode images than untreated areas of the phantom.

The Histotripsy phantoms described herein can have two modes of application: a spatial indicator mode and a dose indicator mode. Spatial mode can give a look at the volume likely to be affected. Red blood cells or other mechanically disruptable (fragile) inclusions (including disruptable dyes or pigments) work well in spatial mode. These types of phantoms show virtually the same spatial indications of damage as real tissue but can be immediately and visually assessed without waiting for histology. The results are also clearly shown in ultrasound imaging, which is the same imaging to be used in vivo.

To obtain a dose phantom, some number of inclusions can be included in the transparent gel, each of which is progressively more resistant to mechanical disruption, even closely paralleling results in specific cells or tissues (i.e., important tissues and cell organelles can be identified along with their sensitivity to mechanical disruption). If "n" of these are identified, there would be "n" different inclusions. Then, for a given dose, or likely the number of pulses at a set intensity, PRF, and pulse width which is sufficient to disrupt 50% of a given structure compared to nearby untreated tissue. A phantom can then be examined (several modes of examination possible) which gives the percent of the different indicators which have been damaged. For example, indicators can be made with damage sensitivities similar to cell membranes, mitochondria, endoplasmic reticulum, and cell nuclei, as well as for complex tissue like vascular capillaries or glandular functional units.

Indicators can be assessed after exposure by looking optically for surviving structures (polymer beads for example) or by the fluorescent dye released with indicator fractionation. Multiple dyes of different color could be assessed in one shot by a spectrophotometer. Ultrasound can give the same image (with the proper phantom) as expected in tissue both treated and untreated.

Therefore, a given tissue under treatment (e.g., prostate or liver) can have a tissue specific phantom which would give some degree of confidence in final clinical result based on exposure and assessment of the phantom.

Methods of using a Histotripsy testing system, such as system 200 of FIG. 2, will now be described. As described above, the Histotripsy testing system can be used for instantaneous verification of the efficacy of transducer and/or acoustic parameter sets, to check on efficacy of acoustic parameter changes, and for testing new transducer spatial/temporal scan patterns and parameters. These methods lend themselves to rapid verification, even in the clinic, of the spatial extent of tissue damage expected for a given set of acoustic and scan parameters.

In one embodiment, a method of testing a Histotripsy transducer comprises applying cavitational ultrasound (e.g., Histotripsy) energy to a Histotripsy phantom and observing a visual change in the Histotripsy phantom. The Histotripsy phantom can be any of the phantoms described herein. For example, the Histotripsy phantom can comprise a transparent or translucent container filled with a gel (such as agarose gel), and can include an indicator disposed in the gel. The cavitational ultrasound (e.g., Histotripsy) energy can be applied by a Histotripsy transducer to the phantom.

In some embodiments, the method can further comprise inserting the phantom into a tank, filling the tank with an acoustic medium (such as degassed water), and directing the cavitational ultrasound (e.g., Histotripsy) energy through the acoustic medium towards the Histotripsy phantom to align a focal point of the Histotripsy transducer with an indicator of the phantom. In some embodiments, the Histotripsy transducer can be mounted to the tank, and the transducer and/or mount can be moved to align the focal point of the transducer with the indicator of the phantom. In other embodiments, the phantom itself can be mounted to the tank, and the phantom can be moved to align the indicator with the focal point of the transducer.

In some embodiments, the method can comprise observing a visual change in the Histotripsy phantom with the naked eye. The Histotripsy phantoms described herein advantageously allow direct visualization of changes to the phantom resulting from application of cavitational ultrasound (e.g., Histotripsy) energy without having to wait for histology. In other embodiments, the method can comprise observing the visual change in the Histotripsy phantom with a camera (such as a high-speed video camera), with an ultrasound imaging system, or with a microscope, for example.

In some embodiments, the method can comprise observing a visual change in a carbon particles indicator. In these embodiments, the areas or "lesions" within the phantom that receive cavitational ultrasound (e.g., Histotripsy) energy will darken in color as energy is applied. The method can comprise observing both efficacy and dosage of the Histotripsy therapy. In other embodiments, the method can comprise observing a visual change in a dye-bead indicator. In these embodiments, the areas or "lesions" within the phantom that receive cavitational ultrasound (e.g., Histotripsy) energy will change in color from transparent or translucent to the color of the dye contained within the beads (e.g., such as red, black, blue, yellow, etc). These methods can comprise observing both efficacy and dosage of the Histotripsy therapy. In yet additional embodiments, the method can comprise observing a visual change in a red blood cells indicator. In these embodiments, the areas or "lesions" within the phantom that receive cavitational ultrasound (e.g., Histotripsy) energy will change in color from red or pink to a lighter shade or to a transparent/translucent color as energy is applied.

In some embodiments, the phantom itself can be designed to resemble either visually or physically an organ or tissue to be treated. For example, the phantom can be shaped or include an indicator shaped to the size and tissue density of a human prostate. Applying energy from the Histotripsy transducer to the prostate shaped indicator can allow the user to test or verify various Histotripsy parameters and dosages before conducting an actual Histotripsy procedure. Other tissue shapes and tissue densities can be formed in the phantom, including shapes and densities similar to the liver, kidney, various tumors such as uterine fibroids, breast fibroadenomas, or carcinoma, for example.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A cavitational damage indicator phantom, comprising:
   a container;
   a gel disposed in the container; and
   an indicator disposed in the container, the indicator configured to change visibly during application of cavitational ultrasound energy to the indicator.

2. The cavitational damage indicator phantom of claim 1 wherein the indicator is embedded between first and second layers of the gel.

3. The cavitational damage indicator phantom of claim 2 wherein the indicator comprises a layer having a thickness of less than 5 mm.

4. The cavitational damage indicator phantom of claim 1 wherein the gel comprises an agarose gel.

5. The cavitational damage indicator phantom of claim 1 wherein the indicator comprises a plurality of carbon particles.

6. The cavitational damage indicator phantom of claim 5 wherein the visible change comprises the carbon particles becoming darker during application of cavitational ultrasound energy to the indicator.

7. The cavitational damage indicator phantom of claim 5 wherein the visible change comprises a breakdown of the size of the carbon particles.

8. The cavitational damage indicator phantom of claim 1 wherein the indicator comprises a plurality of microspheres.

9. The cavitational damage indicator phantom of claim 8 wherein the microspheres comprise polystyrene beads.

10. The cavitational damage indicator phantom of claim 8 wherein the microspheres comprise microencapsulated beads.

11. The cavitational damage indicator phantom of claim 8 wherein the visible change comprises spilling a pigment from the microspheres during application of cavitational ultrasound energy to the indicator.

12. The cavitational damage indicator phantom of claim 1 wherein the indicator comprises red blood cells.

13. The cavitational damage indicator phantom of claim 1 wherein the visible change of the indicator can be detected by a human eye.

14. The cavitational damage indicator phantom of claim 1 wherein the visible change comprises a color change.

15. The cavitational damage indicator phantom of claim 6 wherein the indicator comprises a plurality of layers disposed in the container.

16. The cavitational damage indicator phantom of claim 1 wherein the container is at least partially transparent.

17. The cavitational damage indicator phantom of claim 1 wherein the gel is transparent.

18. The cavitational damage indicator phantom of claim 1 wherein the gel is translucent.

19. A cavitational damage testing system, comprising:
a tank filled with an acoustic medium; and
a cavitational ultrasound phantom disposed in the tank, the cavitational ultrasound phantom comprising a container, a gel disposed in the container, and an indicator disposed in the container, the indicator configured to change visibly under application of cavitational ultrasound energy to the indicator.

20. The cavitational damage testing system of claim 19 wherein the indicator is embedded between first and second layers of the gel.

21. The cavitational damage testing system of claim 20 wherein the indicator comprises a layer having a thickness <5 mm.

22. The cavitational damage testing system of claim 19 wherein the gel comprises a transparent agarose gel.

23. The cavitational damage testing system of claim 19 wherein the indicator comprises a plurality of carbon particles.

24. The cavitational damage testing system of claim 19 wherein the indicator comprises a plurality of microspheres.

25. The cavitational damage testing system of claim 24 wherein the microspheres comprise polystyrene beads.

26. The cavitational damage testing system of claim 24 wherein the microspheres comprise microencapsulated beads.

27. The cavitational damage testing system of claim 19 wherein the indicator comprises red blood cells.

28. The cavitational damage testing system of claim 19 further comprising a mount disposed on or near the tank, the mount configured to receive a cavitational ultrasound transducer.

29. The cavitational damage testing system of claim 28 wherein the mount is configured to align a focal point of the cavitational ultrasound transducer with the cavitational ultrasound phantom.

30. The cavitational damage testing system of claim 19 further comprising a cavitational ultrasound therapy transducer configured to deliver cavitational ultrasound energy to the cavitational ultrasound phantom.

31. The cavitational damage testing system of claim 19 further comprising an imaging system.

32. The cavitational damage testing system of claim 31 wherein the imaging system comprises a high-speed video camera.

33. The cavitational damage testing system of claim 19 wherein the acoustic medium comprises degassed water.

34. A method of testing a Histotripsy transducer, comprising:
applying Histotripsy energy to a Histotripsy phantom; and
observing a visual change in the Histotripsy phantom.

35. The method of claim 34 wherein the visual change comprises a color change.

36. The method of claim 34 wherein the Histotripsy phantom comprises carbon particles disposed in a transparent gel and the visual change comprises observing the carbon particles change to a darker color.

37. The method of claim 34 wherein the Histotripsy phantom comprises microspheres disposed in a transparent gel and the visual change comprises releasing a dye from the microspheres during application of Histotripsy energy to the Histotripsy phantom.

38. The method of claim 34 further comprising, prior to the applying step:
placing the Histotripsy phantom in a testing tank; and
aligning a focal point of a Histotripsy transducer with the Histotripsy phantom.

39. The method of claim 38 wherein the applying Histotripsy energy step comprises applying Histotripsy energy to the Histotripsy phantom with the Histotripsy transducer.

40. The method of claim 34 wherein the Histotripsy phantom resembles a human prostate.

41. The method of claim 34 wherein the visual change observed in the Histotripsy phantom is indicative of tissue damage to be expected during a Histotripsy procedure in a human patient.

* * * * *

UNITED STATES PATENT AND TRADEMARK OFFICE
CERTIFICATE OF CORRECTION

PATENT NO. : 8,539,813 B2
APPLICATION NO. : 12/887705
DATED : September 24, 2013
INVENTOR(S) : Charles A. Cain et al.

Page 1 of 1

It is certified that error appears in the above-identified patent and that said Letters Patent is hereby corrected as shown below:

In the Specification

Column 1, beginning at line 22, after the paragraph following the "Incorporation by Reference" heading and immediately prior to the "Field of the Invention" heading, please insert the following heading and paragraph:

--STATEMENT AS TO FEDERALLY SPONSORED RESEARCH

This invention was made with government support under EB008998 awarded by the National Institutes of Health. The Government has certain rights in the invention.--

Signed and Sealed this
Fourteenth Day of October, 2014

Michelle K. Lee
*Deputy Director of the United States Patent and Trademark Office*